United States Patent [19]  
Smithies et al.

[11] 4,183,911  
[45] Jan. 15, 1980

[54] ANTIPERSPIRANT COMPOSITIONS

[75] Inventors: Barry Smithies, Rochdale; Alan Straw, Macclesfield, both of England

[73] Assignee: Colgate-Palmolive Company, New York, N.Y.

[21] Appl. No.: 472,975

[22] Filed: May 24, 1974

[30] Foreign Application Priority Data

Sep. 18, 1973 [GB] United Kingdom ............... 43699/73

[51] Int. Cl.² ........................ A61K 9/32; A61K 9/36; A61K 9/38; A61K 9/40; B01J 13/00
[52] U.S. Cl. ........................................ 424/36; 424/32; 424/33; 424/35; 424/37; 424/46; 424/47; 252/316
[58] Field of Search ....................... 424/46, 45, 47, 68, 424/37, 32, 36; 252/522, 316

[56] References Cited

U.S. PATENT DOCUMENTS

| 3,088,874 | 5/1963 | Geary et al. | 424/68 X |
| 3,516,941 | 6/1970 | Matson | 252/522 X |
| 3,679,102 | 7/1972 | Charle et al. | 424/47 X |
| 3,691,271 | 9/1972 | Charle et al. | 424/47 X |
| 3,705,102 | 12/1972 | Mast | 252/316 X |
| 3,775,334 | 11/1973 | Christie | 252/316 X |
| 3,798,179 | 3/1974 | Hellyer | 252/316 X |

FOREIGN PATENT DOCUMENTS 987301 3/1965 United Kingdom ...................... 424/47  
1347950 2/1974 United Kingdom ...................... 424/47

OTHER PUBLICATIONS

Schwartz et al., Surface Active Agents & Detergents, 1958, vol. 2, pp. 227-235.

Primary Examiner—Dale R. Ore  
Attorney, Agent, or Firm—Herbert S. Sylvester; Murray M. Grill; Norman Blumenkopf

[57] ABSTRACT

A non-staining antiperspirant spray powder comprises an antiperspirant powder, such as aluminum chlorohydrate, an encapsulated surface active material, such as a liquid, nonionic surface active agent, with the encapsulating material about it being soluble or disruptable by aqueous media and insoluble in the propellant, and a propellant fluid under pressure. The composition is discharged from a container as a powder spray, preferably onto the axilla, by the opening of a discharge valve. The presence of the surface active agent diminishes staining of clothing contacted by the antiperspirant and its encapsulation in a soluble encapsulant allows the gradual release of surface active agent as the aluminum chlorohydrate is activated by the presence of perspiration, while also maintaining the dry character of the powder spray and preventing or diminishing mucous membrane irritation during spraying. Also disclosed are methods for utilization of the described compositions and methods for applying surface active agent to surfaces without causing mucous membrane irritation.

13 Claims, No Drawings

ANTIPERSPIRANT COMPOSITIONS

This invention relates to pressurized antiperspirant spray powders. More particularly, it relates to such a powder which includes an encapsulated surface active material and an unencapsulated antiperspirant, in powder form. Also within the invention are processes for employing such compositions and products and methods of applying surface active agents to human skin and other surfaces.

Antiperspirant sprays which employ aluminum chlorohydrate as the active astringent or antiperspirant ingredient are known and dry powder aerosol antiperspirants based on aluminum chlorohydrate have been marketed. Encapsulated cosmetics, including antiperspirants, have been prepared and powder aerosols in which surface active agents are incorporated to aid in suspending insolubles have been suggested. However, before the present invention it was not known to encapsulate a surface active agent component of an antiperspirant powder aerosol while leaving the active antiperspirant ingredient, e.g., aluminum chlorohydrate, unencapsulated.

If the antiperspirant constituent and surface active agent are both encapsulated the onset of antiperspirant activity due to the active ingredient is delayed and often this is objectionable to the user. Also, larger encapsulated particles will usually result and this can be objectionable because of the greater probability of blocking of the discharge valve passages. When the surface active agent is dissolved or dispersed in the propellant in unencapsulated form, they tend to make the desirably dry powder feel wet to the user. When, to correct these conditions, the surface active agent is omitted from the present antiperspirant powder formulations, it is noted that there is a significantly greater staining effect of the product on clothing which comes into contact with the axillary area to which the antiperspirant powder has been applied. By utilizing the compositions and processes of the present invention, staining may be diminished or prevented and effective antiperspirant activity can be obtained with an aerosol antiperspirant powder that feels dry when applied.

By employing an adhesion or adherence agent in the formulation the dispensed powder can be better held to the skin or other surface to which it is applied, with less loss thereof. Also, the various components of the composition may be maintained sufficiently suspended in the liquefied gas propellant during storage before use by inclusion in the composition of a suspending agent, such as colloidal silica, preferably pyrogenic silica of a particle size less than about one micron. Thus, the invented compositions, products and methods provide solutions to the problems of staining, apparent wetness and valve blocking, one or more of which are often associated with aerosol antiperspirant powders of the prior art.

In accordance with the present invention there is provided a non-staining antiperspirant spray powder composition in a valved container which comprises an antiperspirant powder, an encapsulated surface active material and a propellant fluid under pressure, so that upon opening the container valve there is dischargeable to the atmosphere from the container under the pressure of the fluid a mixture of dry antiperspirant powder and encapsulated surface active agent. Also within the invention are methods of employing such compositions and of applying encapsulated surface active agents to human skin or other surfaces.

The active astringent or antiperspirant material in the antiperspirant powder of the present invention may be any suitable material for such use to prevent or diminish human axillary perspiration. Antiperspirants such as aluminum, zinc and zirconium salts, e.g., aluminum chloride, aluminum sulfate, aluminum sulfamate, zinc chloride, zinc sulfate and zirconium oxychloride, may be employed, at least as a part of the antiperspirant powder component but most preferably the active ingredient utilized will be particulate aluminum chlorohydrate, sometimes referred to as aluminum chlorhydroxide. This material is available in fine powder form, suitable for dispensing through the small valve openings of aerosol spray dispensers. In the present applications particles of the aluminum chlorohydrate will be small, usually having a major or average dimension or diameter in the 10 to 100 micron range, although particles in the 2 to 200 micron range can be employed, providing that they do not agglomerate or block the dispensing valve passageways.

The surface active material of the present compositions may have wetting and/or detersive effects but the wetting agents are preferred. The surface active agent may be anionic, nonionic, cationic or amphoteric but of these the nonionics are most satisfactory and of the nonionics the liquid nonionics have the best stain preventing or diminishing effects. Generally, the surface active agents will include a higher alkyl or fatty acid chain, normally of 10 to 20 carbon atoms and preferably of 12 to 18 carbon atoms and if such is a fatty acid or fatty acid residue chain it will either be saturated or olefinic, preferably with no more than two double bonds in the chain and most preferably of about one double bond. Useful anionic wetting agents that may be employed include linear higher alkyl benzene sulfonates, lower (1-4 carbon atoms) alkyl benzene sulfonates, higher olefin sulfonates, di-middle (7-9 carbon atoms) alkyl sulfosuccinates, ethoxylated higher fatty alcohol sulfates, sulfonates of naphthalene-formaldehyde condensates and higher fatty alcohol and Oxo alcohol sulfates and sulfonates. The salt-forming ion, present to solubilize the surface active material, is preferably an alkali metal, ammonium or lower alkanolamine, e.g., triethanolamine. Although the previously mentioned anionic surface active agents are useful and the cationic surfactants may also be employed, e.g., higher alkyl dimethyl benzyl ammonium chloride, cetyl trimethyl ammonium bromide and distearyl dimethyl ammonium chloride, the preferred nonionic surface active agents, in liquid form, usually constitute all or at least a major proportion of the surface active agent component of the present compositions.

The nonionic surface active agents include the poly-lower alkoxylated, preferably polyethoxylated alcohols, alkyl phenols, esters, acids, amides, sugars and sugar anhydrides, but also include non-alkoxylated nonionics, such as the esters. Normally these will contain from 5 to 200, preferably 5 to 50 moles of ethylene oxide, and the fatty moiety will have from 10 to 20 carbon atoms therein. Preferred embodiments of the nonionic surface active materials include polyoxyethylene sorbitol laurate (Atlas G-1045); polyoxyethylene sorbitol oleate (Atlas G-1186); polyoxyethylene lanolin derivatives (Atlas G-1441); polyoxyethylene oleyl ether (Brij 99, containing 20 moles of ethylene oxide); sorbitan monolaurate (Span 20); sorbitan monooleate (Span 80); polyoxyethylene sorbitan monolaurate (polysorbate 20); polyoxyethylene sorbitan monostearate (polysorbate 60); polyoxyethylene sorbitan monooleate (polysorbate 80); and polyoxyethylene sorbitan trioleate (polysorbate 85); all of which are made by Atlas Chemical Industries Division of ICI America. Also useful are other nonionic surface active agents such as polyethylene glycol ethers of linear alcohols, such as Tergitol 15-S-3; alkyl phenol ethylene oxide adducts (Sterox NE) and octylphenoxy polyethoxy ethanol (Igepal CA-630), which are manufactured, respectively, by Union Carbide Corporation, Monsanto Company and GAF Corporation. Additionally, liquid and in some cases, solid nonionics such as the block copolymers of ethylene oxide and propylene oxide, chain terminated by propylene glycol, and the mixed polymers of ethylene oxide and propylene oxide, may be employed. These are sold under the tradenames Pluronic and Ucon and are manufactured by Wyandotte Chemical Company and Union Carbide Corporation, respectively. Additional descriptions of such compounds, other suitable nonionic surface active agents and various additional surface active compounds, useful in the practice of the present invention are found in McCutcheon's *Detergents and Emulsifiers Annual*, particularly the volumes for 1969–1972.

Any suitable encapsulating material may be employed which is satisfactory under the conditions of storage and use of the present compositions. Thus, it should maintain its form in the pressurized container in contact with the liquefied gas propellant and should allow the contained surface active agent to escape when brought into contact with the skin, perspiration or other aqueous materials on the skin and the other components of the spray powder. Various encapsulating materials of the proteinaceous, cellulosic and synthetic polymer classes may be employed and those preferred and preferably hydrophilic. For example, among the proteinaceous encapsulants the best is gelatin but other amino acid derivatives which have properties like those of proteins may also be utilized. The cellulosic thickeners include synthetic polymers such as sodium carboxymethyl cellulose, hydroxyethylpropyl cellulose and methyl cellulose and such compounds may also be considered to be synthetic organic polymers. Starch compounds are related to the cellulosic materials and corn starch, starch esters and other starch derivatives may be employed. Of the other synthetic organic polymers, polyvinyl alcohol and polyacrylamide are useful. In some cases these materials may be combined with other less hydrophilic polymers to make an encapsulant of the desired properties, film-forming, insoluble in the propellant and soluble in aqueous media on the axilla. Means for effecting encapsulation are well known. Among the descriptions of such methods is that in an article by Herman Nack entitled *Microencapsulation Techniques, Applications and Problems*, published in the Journal of the Society of Cosmetic Chemists at Vol. 21, pages 85-98 Feb. 4, 1970).

The propellants utilized, while they may include compressed gases, are highly preferably limited to the liquefied gases and of these the most preferable are the lower hydrocarbons of 3 to 4 carbon atoms each and the halogenated lower hydrocarbons of 1 to 4 carbon atoms. Mixtures of such materials are also employed to obtain the most desirable dispensing pressures and characteristics. Included among the preferred propellants are propane, isobutane and n-butane. Among the halogenated hydrocarbons those which are chlorofluorinated or fluorinated are preferred. These include trichloromonofluoromethane, dichlorodifluoromethane, dichlorotetrafluoroethane, monochlorodifluoromethane, monochloropentafluoroethane, difluoroethane, monochlorodifluoroethane, trichlorotrifluoroethane and octafluorocyclobutane. Preferred mixtures, to produce most desirable pressures, spraying and dispersing properties are those of isobutane and propane or, even more preferably, trichloromonofluoromethane and dichlorodifluoromethane or dichlorotetrafluoroethane and dichlorodifluoromethane. Various other propellants are described at pages 18-33 of the text *Principles of Aerosol Technology* by Paul A. Sanders, published by Van Nostrand Reinhold Company in 1970. In the same text considerations with respect to the manufacture of aerosol powders are set forth at pages 311-320. Various suitable containers, valves and adjuvant materials are also described in the text.

The colloidal silica utilized to maintain the aluminum chlorohydrate and encapsulated surface active material suspended in the composition before use is preferably a pyrogenic silica but other types of silica particles of colloidal sizes may be employed. The colloidal silica will normally by of particle size less than 100 millimicrons, preferably averaging less than 50 mmm. in diameter. Among the more preferred pyrogenic silicas the diameters will be in the 2 to 20 mmm. range and often the ultimate particle size of a preferred pyrogenic silica, such as that sold by Cabot Corporation, Boston, Mass., as Cab-O-Sil M-5, will have an ultimate particle diameter of about 11 mmm. whereas the corresponding H-5 grade has a diameter of about 7 mmm. The surface areas of the pyrogenic colloidal silicas and other colloidal silicas having average particle sizes less than one micron are exceptionally great, often ranging from about 50 to 500 square meters per gram, leading to their desirable thickening, suspending, and covering properties. The particles are also of generally spherical shape.

The adherence promoting agent in the composition is usually a higher fatty compound, such as a higher fatty acid ester of a lower alkanol. The higher fatty acid has 12 to 18 carbon atoms in the molecule and the lower alcohol is normally of from 1 to 4 carbon atoms, preferably of 2 to 3. Among the best of these materials is isopropyl myristate but mixed fatty acid esters of isopropanol, n-propanol and ethanol may also be employed. Similarly, cetyl alcohol derivatives and other "fatty" substances which promote adherence of the powder to the skin, without making the skin feel wet or sticky, may be employed.

Of course, various adjuvants may be utilized but normally these will not be encapsulated, although in some instances minor adjuvants may also be encapsulated with the surface active agent, especially, if they tend to be of very small particle size or otherwise irritating in use. Among the adjuvants employed may be mentioned, perfumes, bactericides, fungicides, emollients and other skin treating materials.

The propellant and other constituents utilized will contain as little water as feasible, most preferably being anhydrous and preferably containing less than 0.1% of moisture, although in some instances as much as 1% of moisture may be tolerable. Encapsulated surface active agent, in encapsulated form, will normally be of about the same particle sizes as the aluminum chlorohydrate or antiperspirant powder particles, both generally being in the 10 to 100 micron diameter range, preferably 30 to 60 microns. The encapsulated surface active agent, including encapsulant, will usually be from 10 to 90% surface active agent and 90 to 10% of encapsulating material, often from 30 to 70% and 70 to 30% and preferably about equal parts of each are present.

The proportions of the various constituents in the pressurized composition are variable to suit the particular circumstances but normally they will be from 1 to 7% of antiperspirant powder, from 0.1 to 3% of encapsulated surface active material and from 75 to 95% of propellant. Such figures do not include the encapsulant. Instead of percentages, parts by weight may be employed, when other materials are also present. Preferably, when the antiperspirant is aluminum chlorohydrate and otherwise, it will be from 1.5 to 5%, the encapsulated nonionic surface active agent will be from 0.5 to 3%, the encapsulating material will be from 0.1 to 10%, there will be present from 0.1 to 2% of colloidal silica and 0.5 to 10% adhesion or adherence agent and the liquefied gas propellant will be from 80 to 92%. The pressure generated by the propellant will generally be at least 10 lbs./sq. in. and will normally be from 20 to 100 lbs./sq. in., preferably about 30 to 50 lbs./sq. in.

To employ the powder aerosol antiperspirant it is only necessary to depress or otherwise open the dispensing valve and allow a spray of the dry powder to be directed onto a body surface from which perspiration normally is released, e.g., an axilla. Normal quantities of the powder are employed and it is dispensed at approximately room temperature. Because the propellant evaporates before contacting the skin, the powder does not have an objectionably severe cooling effect.

After the powder is deposited on the skin, with the adherence agent helping it to be maintained thereon, when perspiration is generated the aluminum chlorohydrate is activated and exerts an astringent effect. Simultaneously, the encapsulated surface active agent is released and mixes with the astringent and perspiration. Its presence aids in preventing staining of clothing contacting such perspiration and the antiperspirant and when the clothing or garment is washed any stains are more readily released from it.

The following examples illustrate the invention. Unless otherwise mentioned, all parts are by weight and all temperatures are in °C.

EXAMPLE 1

| | Parts by Weight |
|---|---|
| Aluminum chlorohydrate | 3.0 |
| Encapsulated Ethylan BCP (50:50 surface active agent: gelatin. Ethylan BCP is a nonylphenol ethoxylate containing about 9 moles ethylene oxide, made by Lankro Chemicals Ltd., Eccles, Manchester, England) | 3.0 |
| Pyrogenic silica (Cab-O-Sil M-5) | 0.2 |
| Isopropyl myristate | 6.6 |
| Perfume | 0.2 |
| Propellant mixture (60:40 Propellants 11:12) | 87.0 |

The product is made by mixing together in the dispensing container all the components except for the propellant mixture, stacking the valve unit to the container and gassing the container with the propellant mixture by back-feeding it through the discharge valve. The aluminum chlorohydrate particles are of an average of about 50 microns in diameter and the encapsulated Ethylan BCP particles are of about the same size.

Immediately after filling the product it is ready for use. To employ it there are discharged to each of the axilla of a normally heavy sweating male adult two-second sprays, which deposit about 0.06 gram of encapsulated surface active agent on each of the axilla, together with about the same quantity of aluminum chlorohydrate. Almost immediately an astringent action is noted when the axilla are moist or are moistened by perspiration, and effective antiperspirant action results. Compared to a similar formulation not containing the encapsulated surface active agent the stainings of portions of clothing and garments contacting the axillae are much less. Also, compared with the same formula wherein the surface active agent is present but is not encapsulated, less irritation of the nasal passages, the eyes and other mucous membranes is observed with the experimental formula. This is apparently because the droplets of nonionic surfactant formed by evaporation of the propellant are smaller and more likely to contact the membranes when not encapsulated. The discharge valve does not plug and excessive settling of product is not observed with the invented compositions. The proportion of aluminum chlorohydrate in the product is about constant during repeated sprayings and the aerosol powder antiperspirant feels dry when applied, although it contains a liquid surface active agent.

When an ordinary aerosol powder antiperspirant is utilized and the encapsulated surface active agent described is discharged from another aerosol composition in a dispensing container which includes only isopropyl myristate and propellant, in addition to the encapsulated surface active agent, the presence of the encapsulated surface active agent on the skin helps to diminish staining caused by perspiration and the presence of the aluminum chlorohydrate. It appears that staining of cottons and other fabrics by perspiration, body soil and even by the adherence promoting agents and emollients in the antiperspirant is much more severe (often three times as great) when the encapsulated surface active agent is omitted. Also, compared to similar compositions in which the surface active agent is present but is not encapsulated, much less irritation is noted at the mucous membranes and passages.

EXAMPLE 2

| | Parts by Weight |
|---|---|
| Aluminum chlorohydrate | 3.0 |
| Encapsulated Ethylan BCP | 3.0 |
| Pyrogenic silica (Cab-O-Sil M-5) | 0.2 |
| Isopropyl myristate | 1.8 |
| Perfume | 0.2 |
| Isopar 687 LCL (a branched chain $C_{11}$—$C_{13}$ saturated hydrocarbon supplied by Esso, England - an adherence promoting agent) | 4.8 |

EXAMPLE 3

| | Parts by Weight |
|---|---|
| Aluminum chlorohydrate | 3.0 |
| Encapsulated Ethylan BCP | 3.0 |
| Pyrogenic silica (Cab-O-Sil M-5) | 0.2 |
| Fluid AP (a polyalkylene oxide adduct of n-butanol the alkyls being a mixture of ethyl and propyl groups, supplied by Union Carbide) | 2.4 |
| Antarox CO 630 (a nonylphenol ethoxylate, a nonionic surface active | |

-continued

| | Parts by Weight |
|---|---|
| agent, supplied by G.A.F. Limited, England) | 2.4 |
| Perfume | 0.2 |

EXAMPLE 4

| | Parts by Weight |
|---|---|
| Aluminum chlorohydrate | 3.0 |
| Encapsulated Ethylan BCP | 3.0 |
| Pyrogenic silica (Cab-O-Sil M-5) | 0.2 |
| Emcol F 26–46 (a polymeric ester of oleic acid that conforms generally to the formula: $$CH_3(CH_2)_7CH{=}CH(CH_2)_7\overset{O}{\overset{\|}{C}}O(\underset{\underset{CH_3}{\|}}{C}HCH_2O)_nH$$ where n has an average value of 36 | 6.6 |
| Perfume | 0.2 |

The invention has been described with respect to various illustrative and working examples thereof but is not to be limited to these since it is evident that one of skill in the art, with the present specification and claims before him, may be able to utilize substitutes and equivalents without departing from the spirit of the invention.

What is claimed is:

1. A non-staining antiperspirant spray powder composition in a valved container, comprising 1 to 7% of an unencapsulated, powdered aluminum, zinc, or zirconium antiperspirant salt having a particle size of 2 to 200 microns, 0.1 to 3% of an encapsulated surface active material selected from the group consisting of anionic, nonionic, cationic and amphoteric surfactants and a propellant fluid under pressure.

2. An antiperspirant spray powder composition according to claim 1 wherein the antiperspirant powder is aluminum chlorohydrate, the encapsulated surface active material is a nonionic surface active agent, it is encapsulated by a coating material which is insoluble in the propellant.

3. An antiperspirant spray powder composition according to claim 2 which is anhyrous and wherein the encapsulating material is soluble in aqueous media.

4. An antiperspirant spray powder composition acccording to claim 1 which includes from 75 to 95% of propellant.

5. An antiperspirant spray powder composition according to claim 3 which comprises from 1.5 to 5% of aluminum chlorohydrate, 0.5 to 3% of encapsulated nonionic surface active agent, 0.1 to 10% of encapsulating material, 0.1 to 2% of colloidal silica, 0.5 to 10% of an adhesion agent which is an ester of a $C_{1-4}$ alkanol and a $C_{12-18}$ fatty acid and 80 to 92% of liquefied gas propellant.

6. An antiperspirant spray powder composition according to claim 5 wherein the nonionic surface active agent is a polyoxyethylene derivative, the encapsulating material is hydrophilic proteinaceous, the colloidal silica is pyrogenic silica, and the liquefied gas propellant is a mixture of lower hydrocarbons of 3 to 4 carbon atoms, a mixture of lower halogenated hydrocarbons of 1 to 4 carbon atoms, wherein the halogens and fluorine and/or chlorine or a mixture of such lower hydrocarbons and lower halogenated hydrocarbons, said mixture generating a pressure in the container of from 20 to 100 lbs./sq. in.

7. An antiperspirant spray powder composition according to claim 6 wherein the nonionic surface active agent is polyoxyethylene sorbitan monooleate, the encapsulating material is gelatin, the colloidal silica is of particle sizes averaging less than one micron, the aluminum chlorohydrate and encapsulated nonionic surface active agent particles are of maximum dimensions in the 10 to 100 micron range, the adhesion agent is isopropyl myristate and the liquefied gas propellant is a mixture of chlorofluorohydrocarbons.

8. An antiperspirant spray powder composition according to claim 7 which comprises about three parts of aluminum chlorohydrate, and three parts of encapsulated polyoxyethylene sorbitan monooleate encapsulated in gelatin with the proportions of nonionic surface active agent and encapsulating material being about 1:1 and the three parts including the gelatin 0.2 part of pyrogenic silica 6.6 parts of isopropyl myristate, 0.2 part of perfume and 87 parts of a 60:40 mixture of trichloromonofluoromethane and dichlorodifluoromethane.

9. An antiperspirant spray powder composition according to claim 1 wherein said salt is selected from the group consisting of aluminum chloride, aluminum sulfate, aluminum sulfamate, zinc chloride, zinc sulfate, zirconium oxychloride and aluminum chlorhydroxide.

10. An antiperspirant spray powder composition according to claim 1 wherein said surface active material includes a $C_{10-20}$ alkyl or $C_{12-18}$ fatty acid residue chain.

11. An antiperspirant spray powder composition according to claim 1 wherein said anionic surface active material is selected from the group consisting of linear higher alkyl benzene sulfonates, $C_{1-4}$ alkyl benzene sulfonates, higher olefin sulfonates, di $C_{7-9}$ alkyl sulfosuccinates, ethoxylated higher fatty alcohol sulfates, sulfonates of naphthalene-formaldehyde condensates and higher fatty alcohol, oxo alcohol sulfates and sulfonates.

12. An antiperspirant spray powder composition according to claim 1 wherein said nonionic surface active material is selected from the group consisting of polyoxyethylene sorbitol higher fatty acid esters, polyethylene glycol ethers of linear alcohols and block copolymers of ethylene oxide and propylene oxide.

13. An antiperspirant spray powder composition according to claim 1 wherein said cationic surface active material is selected from the group consisting of higher alkyl dimethyl benzyl ammonium chloride, cetyl trimethyl ammonium bromide and distearyl dimethyl ammonium chloride.

* * * * *